(12) United States Patent
Salisbury et al.

(10) Patent No.: US 7,390,919 B1
(45) Date of Patent: Jun. 24, 2008

(54) METHYL ACETATE PURIFICATION AND CARBONYLATION

(75) Inventors: Brian A. Salisbury, Oxford, PA (US); Ronnie M. Hanes, Huntsville, AL (US); Noel C. Hallinan, Loveland, OH (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/906,313

(22) Filed: Oct. 1, 2007

(51) Int. Cl.
*C07C 67/48* (2006.01)

(52) U.S. Cl. ..................................... 560/248

(58) Field of Classification Search .................. None
See application file for complete search history.

(56) References Cited

U.S. PATENT DOCUMENTS

| | | | |
|---|---|---|---|
| 5,620,567 A | 4/1997 | Seidel et al. | |
| 5,817,869 A | 10/1998 | Hinnenkamp et al. | |
| 5,932,764 A | 8/1999 | Morris et al. | |
| 7,208,625 B1 | 4/2007 | Wang et al. | |

*Primary Examiner*—Paul A Zucker
(74) *Attorney, Agent, or Firm*—Shao-Hua Guo

(57) ABSTRACT

Disclosed is a method for removing aldehyde impurities from a methyl acetate supply. The method comprises reacting the methyl acetate supply with a polyol and converting the aldehyde impurities to cyclic acetals. The acetals are subsequently removed from the methyl acetate supply by, e.g., distillation. The purified methyl acetate supply is used for carbonylation to produce acetic acid.

16 Claims, No Drawings

US 7,390,919 B1

METHYL ACETATE PURIFICATION AND CARBONYLATION

FIELD OF THE INVENTION

The invention relates to methyl acetate purification. More particularly, the invention relates to removing aldehyde impurities from a methyl acetate supply and using the purified methyl acetate supply for carbonylation.

BACKGROUND OF THE INVENTION

Carbonylation of methanol produces acetic acid. Prior to 1970, acetic acid was made using cobalt catalysts. A rhodium carbonyl iodide catalyst was developed in 1970 by Monsanto. The rhodium catalyst is considerably more active than the cobalt catalyst. Most importantly, the rhodium catalyst gives high selectivity to acetic acid.

One problem associated with the original Monsanto process is that a large amount of water (about 14%) is needed to produce hydrogen in the reactor via the water-gas shift reaction. Water and hydrogen are needed to react with precipitated Rh(III) and inactive [RhI$_4$(CO)$_2$] to regenerate the active Rh(I) catalyst. The large amount of water increases the amount of hydrogen iodide, which is highly corrosive and leads to engineering problems.

Millennium Petrochemical Company developed a new rhodium carbonylation catalyst system. The catalyst system uses a pentavalent Group VA oxide such as triphenylphosphine oxide as a catalyst stabilizer. The catalyst system not only reduces the amount of water needed but also increases the carbonylation rate and acetic acid yield. See U.S. Pat. No. 5,817,869.

One challenge still facing the industry is that lowering water concentration in the methanol carbonylation results in increased aldehyde formation. Methods for reducing aldehyde concentration in acetic acid are known. For instance, U.S. Pat. No. 7,208,625 teaches reducing aldehyde and other permanganate-reducing impurities from acetic acid by contacting acetic acid with peracetic acid and air. Co-pending application Ser. Nos. 11/496,900 and 11/508,109 teaches removing aldehyde impurities from acetic acid by reacting the aldehydes with hydroxyl compounds to form acetals which are then removed from acetic acid by distillation. Co-pending application Ser. No. 11/810,167 teaches extracting the aldehyde impurities with a polyol from a methyl iodide solution in the acetic acid production process.

Methyl acetate is commonly used in methanol carbonylation. One source of methyl acetate is the byproducts of polyvinyl acetate hydrolysis or methanolysis. These byproducts are often supplied as mixtures of methyl acetate and methanol and they contain various amounts of aldehyde impurities. It is important to remove aldehyde impurities from the methyl acetate supply because these impurities complicate the methanol carbonylation and increase the impurity level in the acetic acid product. However, some aldehyde impurities, such as acetaldehyde, are not easy to separate from methyl acetate because of their close boiling points. Thus, new methods for removing aldehyde impurities from methyl acetate are needed.

SUMMARY OF THE INVENTION

The invention is a method for removing aldehyde impurities from a methyl acetate supply. The methyl acetate supply can be methyl acetate or mixtures of methyl acetate and methanol. The method comprises reacting aldehyde impurities with a polyol to form cyclic acetals that can be readily isolated from the methyl acetate supply by, e.g., distillation. The purified methyl acetate supply can be used in carbonylation to produce acetic acid.

DETAILED DESCRIPTION OF THE INVENTION

The invention is a method for removing an aldehyde impurity from a methyl acetate supply. The method comprises reacting the methyl acetate supply with a polyol and converting the aldehyde to a cyclic acetal which can be readily removed from the methyl acetate supply by, e.g., distillation. Suitable methyl acetate supply includes methyl acetate and mixtures of methyl acetate and methanol. Mixtures of methyl acetate and methanol are available from polyvinyl acetate hydrolysis and methanolysis. These mixtures usually contain from about 40 wt % to about 60 wt % of methyl acetate. The methyl acetate supply contains preferably from about 50 ppm to about 5 wt %, more preferably from about 50 ppm to about 1,000 ppm, and most preferably from about 100 ppm to about 500 ppm, of aldehyde impurities. Examples of aldehyde impurities include acetaldehyde, crotonaldehyde, butyraldehyde, their derivatives such as 2-ethyl crotonaldehyde, 2-ethyl butyraldehyde, the like, and mixtures thereof. The aldehyde impurities are typically acetaldehyde and butyraldehyde.

Suitable polyols include those which have at least two hydroxyl groups per molecule and form cyclic acetals with the aldehyde impurities. Suitable polyols have 2 to 10 carbon atoms. Examples include ethylene glycol, propylene glycol, 1,4-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, and neopentyl glycol, the like, and mixtures thereof. Ethylene glycol and 2-methyl-1,3-propanediol are preferred because they are inexpensive and readily available. 2-Methyl-1,3-propanediol is particularly preferred.

Aldehydes react with the polyols to form cyclic acetals. For instance, acetaldehyde reacts with 2-methyl-1,3-propanediol to form 2,4-dimethyl-1,3-dioxane. The cyclic acetals have significantly higher boiling points than methyl acetate or methanol and thus they can be readily removed from methyl acetate or mixtures of methyl acetate and methanol by distillation.

Preferably, the above reaction is performed at a temperature within the range of about 20° C. to about 135° C. More preferably, the temperature is within the range of about 20° C. to about 50° C. Preferably, the reaction is performed in the presence of an acid catalyst. More preferably, the acid catalyst is an ion exchange resin.

Preferably, the polyol is used in an amount within the range of about 1 equivalent to about 10 equivalents of the aldehyde impurities. More preferably, the polyol is used in an amount within the range of about 1 equivalent to about 5 equivalents of the aldehyde impurities. The method of the invention can convert greater than 99.9% of the aldehyde impurity of the methyl acetate supply to cyclic acetals. The excess amount of polyol can be separated from the methyl acetate supply by distillation.

The purified methyl acetate supply can be used for carbonylation to produce acetic acid. The carbonylation can be performed by feeding methanol, carbon monoxide, and the purified methyl acetate supply to the carbonylation reactor. Preferably, the methyl acetate supply is fed in an amount from about 2 wt % to about 20 wt % of the carbonylation reaction medium. More preferably, the methyl acetate supply is fed in an amount from about 2 wt % to about 16 wt % of the carbonylation reaction medium. Most preferably, the methyl acetate supply is fed in an amount from about 2 wt % to about 8 wt % of the carbonylation reaction medium. The use of the purified methyl acetate supply reduces the aldehyde impurity level in the acetic acid product and increases the carbonylation efficiency.

The carbonylation reaction is usually performed in the presence of both a carbonylation catalyst and a catalyst stabilizer. Suitable carbonylation catalysts include those known in the acetic acid industry. Examples of suitable carbonylation catalysts include rhodium catalysts and iridium catalysts. Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $HRh(CO)_2I_2$, the like, and mixtures thereof. Most preferably, the rhodium compounds are selected from the group consisting of $HRh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates. The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds.

Preferably, the carbonylation reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is performed in the presence of water. Preferably, the concentration of water present is from about 2 wt % to about 14 wt % of the carbonylation reaction medium. More preferably, the water concentration is from about 2 wt % to about 10 wt %. Most preferably, the water concentration is from about 4 wt % to about 8 wt %.

Preferably, the carbonylation reaction is performed in the presence of methyl iodide. Methyl iodide is a catalyst promoter. Preferably, the concentration of methyl iodide is from about 0.6 wt % to about 36 wt % of the carbonylation reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide.

Hydrogen may also be fed into the carbonylation reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

The following examples merely illustrate the invention. Those skilled in the art will recognize many variations that are within the spirit of the invention and scope of the claims.

EXAMPLE 1

A 50/50 methanol/methyl acetate mixture which contains 2 wt % of acetaldehyde (50 g) and Amberlyst 15 (6 g) are added to a 100-mL flask at room temperature (25° C.). The flask contents are stirred for one minute and 2-methyl-1,3-propanediol (10 g) is then added to the flask via pipette. The resultant flask contents are stirred for 15 minutes and samples are taken for gas chromatographic analysis (GC). The GC analysis indicates that after 15 minutes of reaction greater than 99.9% of acetaldehyde is converted to 2,4-dimethyl-1,3-dioxane (99.1 wt %) and acetaldehyde dimethylacetal (0.9 wt %). After 45 minutes of reaction the acetal product distribution is: 99.5% of 2,4-dimethyl-1,3-dioxane and 0.5% of acetaldehyde dimethylacetal.

EXAMPLE 2

The general procedure of Example 1 is followed. A 50/50 methanol/methyl acetate mixture which contains 2,000 ppm of acetaldehyde (50 g) and Amberlyst 15 (5 g) are added to the flask. The flask contents are stirred for one minute and 2-methyl-1,3-propanediol (1 g) is then added to the flask via pipette. The resultant flask contents are stirred for 15 minutes and samples are taken for gas chromatographic analysis (GC). The GC analysis indicates that after 15 minutes of reaction greater than 99.9% of acetaldehyde is converted to 2,4-dimethyl-1,3-dioxane (84.3 wt %) and acetaldehyde dimethylacetal (15.7 wt %). After 45 minutes of reaction the acetal product distribution is: 85.6 wt % of 2,4-dimethyl-1,3-dioxane and 14.4 wt % of acetaldehyde dimethylacetal.

EXAMPLE 3

The general procedure of Example 1 is followed. A 50/50 methanol/methyl acetate mixture which contains 1,000 ppm of acetaldehyde (50 g) and Amberlyst 15 (5 g) are added to the flask. The flask contents are stirred for one minute and then 2-methyl-1,3-propanediol (0.51 g) is added to the flask via pipette. The resultant flask contents are stirred for 15 minutes and samples are taken for gas chromatographic analysis (GC). The GC analysis indicates that after 15 minutes of reaction greater than 99.9% of acetaldehyde is converted to 2,4-dimethyl-1,3-dioxane (68.4 wt %) and acetaldehyde dimethylacetal (31.6 wt %). After 45 minutes of reaction the acetal product distribution is: 70.1 wt % of 2,4-dimethyl-1,3-dioxane and 29.9 wt % of acetaldehyde dimethylacetal.

EXAMPLE 4

The general procedure of Example 1 is followed. A 50/50 methanol/methyl acetate mixture which contains 300 ppm of acetaldehyde (50 g) and Amberlyst 15 (5 g) are added to the flask. The flask contents are stirred for one minute and then 2-methyl-1,3-propanediol (0.15 g) is added to the flask via pipette. The resultant flask contents are stirred for 15 minutes and samples are taken for gas chromatographic analysis (GC). The GC analysis indicates that after 15 minutes of reaction greater than 99.9% of acetaldehyde is converted to 2,4-dimethyl-1,3-dioxane (67.7 wt %) and acetaldehyde dimethylacetal (32.4 wt %). After 45 minutes of reaction the acetal product distribution is: 64.6 wt % of 2,4-dimethyl-1,3-dioxane and 35.4 wt % of acetaldehyde dimethylacetal.

EXAMPLE 5

An ATR (attenuated total reflectance) infrared probe, coupled via optic conduit to an infrared spectrometer, is inserted into a flask. Amberlyst 15 (0.25 g) and an acetonitrile solution (3.3 mL) containing 1 mol/L of acetaldehyde and 1 mol/L of ethylene glycol are added to the flask. The flask contents are allowed to sit for about 12 minutes at room temperature (25° C.) and an infrared spectrum is then obtained. The formation of cyclic acetal is indicated by the absorption band at 1140 cm$^{-1}$. After 12 minutes, 91% of acetaldehyde has reacted with ethylene glycol and has been converted to the corresponding acetal.

This experiment is repeated with glycerin, 1,3-propanediol, and 1,4-butanediol. The results in Table 1 indicate that these polyols are all capable of reacting with acetaldehyde to form corresponding acetals.

TABLE 1

Reaction of Polyols with Acetaldehyde

| Polyol | Conversion of Acetaldehyde to Acetal |
|---|---|
| Ethylene Glycol | 91% |
| Glycerin | 100% |
| 1,3-Propanediol | 100% |
| 1,4-Butanediol | 79% |

We claim:

1. A method for removing an aldehyde impurity from a methyl acetate supply, said method comprising reacting the supply with a polyol to convert the aldehyde to a cyclic acetal, and isolating the acetal from the methyl acetate supply.

2. The method of claim 1, wherein the polyol is a $C_2$-$C_{10}$ diol or triol.

3. The method of claim 1, wherein the polyol is selected from the group consisting of ethylene glycol, propylene glycol, 1,4-butanediol, 1,3-butanediol, 1,3-propanediol, 2-methyl-1,3-propanediol, 2,2-dimethyl-1,3-propanediol, cyclohexane-1,4-dimethanol, glycerin and mixtures thereof.

4. The method of claim 1, wherein the polyol is selected from the group consisting of 1,3-propanediol, 2-methyl-1,3-propanediol, and glycerin.

5. The method of claim 1, wherein the methyl acetate supply is a mixture of methyl acetate and methanol.

6. The method of claim 1, wherein the aldehyde impurity comprises acetaldehyde.

7. The method of claim 6, wherein the methyl acetate supply contains from about 50 ppm to about 50,000 ppm acetaldehyde.

8. The method of claim 7, wherein the methyl acetate supply contains from about 50 ppm to about 1000 ppm acetaldehyde.

9. The method of claim 1, wherein the reaction is performed in the presence of an acidic catalyst.

10. The method of claim 9, wherein the catalyst is an ion exchange resin.

11. The method of claim 1, wherein the acetal is isolated from the methyl acetate supply by distillation.

12. A methanol carbonylation process comprising carbonylating methanol in the presence of a carbonylation catalyst, a catalyst stabilizer, and a methyl acetate supply purified by the method of claim 1.

13. The process of claim 12, wherein the carbonylation catalyst is selected from the group consisting of rhodium catalysts and iridium catalysts.

14. The process of claim 12, wherein the catalyst stabilizer is a phosphine oxide.

15. The method of claim 12, wherein the catalyst stabilizer is triphenylphosphine oxide.

16. The method of claim 12, wherein the catalyst stabilizer is lithium iodide.

* * * * *